(12) United States Patent
Fredrickson et al.

(10) Patent No.: US 11,701,448 B2
(45) Date of Patent: *Jul. 18, 2023

(54) POWDER FOR ACHIEVING HEMOSTASIS

(71) Applicant: Boston Scientific Scimed, Inc., Maple Grove, MN (US)

(72) Inventors: Gerald Fredrickson, Westford, MA (US); Amanda L. Smith, Boston, MA (US); Andrew Pic, Northborough, MA (US); Sophia Gervasio, Coventry, RI (US); Lauren Lydecker, Millbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 350 days.

This patent is subject to a terminal disclaimer.

(21) Appl. No.: 17/002,399

(22) Filed: Aug. 25, 2020

(65) Prior Publication Data

US 2020/0384148 A1 Dec. 10, 2020

Related U.S. Application Data

(63) Continuation of application No. 16/245,780, filed on Jan. 11, 2019, now Pat. No. 10,786,596.

(60) Provisional application No. 62/616,751, filed on Jan. 12, 2018.

(51) Int. Cl.
| | | |
|---|---|---|
| *A61L 31/16* | (2006.01) | |
| *A61L 26/00* | (2006.01) | |
| *A61K 31/722* | (2006.01) | |
| *A61L 31/04* | (2006.01) | |
| *A61M 25/09* | (2006.01) | |

(52) U.S. Cl.
CPC ........ *A61L 26/0023* (2013.01); *A61K 31/722* (2013.01); *A61L 26/008* (2013.01); *A61L 26/0066* (2013.01); *A61L 31/042* (2013.01); *A61L 31/16* (2013.01); *A61L 2300/232* (2013.01); *A61L 2300/418* (2013.01); *A61L 2300/60* (2013.01); *A61L 2400/04* (2013.01); *A61M 25/09* (2013.01); *A61M 2025/091* (2013.01); *A61M 2202/064* (2013.01); *A61M 2210/1042* (2013.01)

(58) Field of Classification Search
CPC combination set(s) only.
See application file for complete search history.

(56) References Cited

U.S. PATENT DOCUMENTS

| | | |
|---|---|---|
| 471,854 A | 3/1892 | Howard |
| 881,238 A | 3/1908 | Hasbrouck |
| 1,145,520 A | 7/1915 | Smith |
| 1,599,959 A | 9/1926 | Buheiji |
| 1,732,566 A | 10/1929 | McKendrick |
| 2,151,418 A | 3/1939 | Bolte |
| 2,185,927 A | 6/1940 | Shelanski |
| 2,478,715 A | 8/1949 | Schmitt |
| 2,623,519 A | 12/1952 | Cohen |
| 3,669,113 A | 6/1972 | Altounyan et al. |
| 3,940,061 A | 2/1976 | Gimple et al. |
| 4,184,258 A | 6/1980 | Barrington et al. |
| 4,427,450 A | 1/1984 | Kostansek |
| 4,457,329 A | 7/1984 | Werley et al. |
| 4,806,167 A | 2/1989 | Raythatha |
| 5,215,221 A | 6/1993 | Dirksing |
| 5,231,983 A | 8/1993 | Matson et al. |
| 5,273,531 A | 12/1993 | Knoepfler |
| 5,312,331 A | 5/1994 | Kneopfler |
| 5,312,333 A | 5/1994 | Churinetz et al. |
| 5,366,122 A | 11/1994 | Guentert et al. |
| 5,445,612 A | 8/1995 | Terakura et al. |
| 5,470,311 A | 11/1995 | Setterstrom et al. |
| 5,599,916 A | 2/1997 | Dutkiewicz et al. |
| 5,622,721 A | 4/1997 | Dansereau et al. |
| 5,884,621 A | 3/1999 | Matsugi et al. |
| 5,902,798 A | 5/1999 | Gouda et al. |
| 5,951,531 A | 9/1999 | Ferdman et al. |
| 6,003,512 A | 12/1999 | Gerde |

(Continued)

FOREIGN PATENT DOCUMENTS

| | | |
|---|---|---|
| CN | 101401956 A | 4/2009 |
| CN | 102241837 A | 11/2011 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

(Continued)

*Primary Examiner* — Ali Soroush
(74) *Attorney, Agent, or Firm* — Bookoff McAndrews, PLLC

(57) ABSTRACT

In various aspects, the present disclosure pertains to methods of treating or preventing bleeding at a tissue site comprising applying a chitosan powder composition to the tissue site. In various aspects, the present disclosure pertains to chitosan powder compositions for application to a tissue site, where the powder compositions comprise a chitosan salt, a crosslinked chitosan, a derivatized chitosan, or a combination thereof. In various aspects, the disclosure pertains to catheter assemblies, which are preloaded with a chitosan powder composition and which are configured to deliver the chitosan powder composition a tissue site.

20 Claims, No Drawings

(56) References Cited

U.S. PATENT DOCUMENTS

| | | |
|---|---|---|
| 6,484,750 B1 | 11/2002 | Foos et al. |
| 6,554,022 B2 | 4/2003 | Wakeman |
| 6,589,087 B2 | 7/2003 | Mackal et al. |
| 6,684,917 B2 | 2/2004 | Zhu et al. |
| 6,708,712 B2 | 3/2004 | Wakeman |
| 6,716,190 B1 | 4/2004 | Glines et al. |
| 6,799,571 B1 | 10/2004 | Hughes et al. |
| 7,178,547 B2 | 2/2007 | Mackal |
| 7,311,270 B2 | 12/2007 | Kapila |
| 7,334,598 B1 | 2/2008 | Hollars |
| 7,361,300 B2 | 4/2008 | Kelly et al. |
| 7,427,607 B2 | 9/2008 | Suzuki |
| 7,455,248 B2 | 11/2008 | Kablik et al. |
| 7,461,649 B2 | 12/2008 | Gamard et al. |
| 7,544,177 B2 | 6/2009 | Gertner |
| 7,563,299 B2 | 7/2009 | Baptista da Costa et al. |
| 7,673,647 B2 | 3/2010 | Mackal |
| 7,841,338 B2 | 11/2010 | Dunne et al. |
| 7,892,205 B2 | 2/2011 | Palasis et al. |
| 7,921,874 B2 | 4/2011 | Tekulve et al. |
| 8,037,880 B2 | 10/2011 | Zhu et al. |
| 8,097,071 B2 | 1/2012 | Burgess et al. |
| 8,118,777 B2 | 2/2012 | Ducharme et al. |
| 8,269,058 B2 | 9/2012 | McCarthy et al. |
| 8,313,474 B2 | 11/2012 | Campbell et al. |
| 8,360,276 B2 | 1/2013 | Rogier et al. |
| 8,361,054 B2 | 1/2013 | Ducharme et al. |
| 8,496,189 B2 | 7/2013 | Lomond et al. |
| 8,673,065 B2 | 3/2014 | Burgess et al. |
| 8,703,176 B2 | 4/2014 | Zhu et al. |
| 8,721,582 B2 | 5/2014 | Ji |
| 8,728,032 B2 | 5/2014 | Ducharme et al. |
| 8,741,335 B2 | 6/2014 | McCarthy |
| 8,827,980 B2 | 9/2014 | Ji |
| 8,910,627 B2 | 12/2014 | Iwatschenko et al. |
| 8,951,565 B2 | 2/2015 | McCarthy |
| 9,028,437 B2 | 5/2015 | Ott et al. |
| 9,089,658 B2 | 7/2015 | Dunne et al. |
| 9,101,744 B2 | 8/2015 | Ducharme |
| 9,107,668 B2 | 8/2015 | Melsheimer et al. |
| 9,132,206 B2 | 9/2015 | McCarthy |
| 9,204,957 B2 | 12/2015 | Gregory et al. |
| 9,205,170 B2 | 12/2015 | Lucchesi et al. |
| 9,205,207 B2 | 12/2015 | Ji |
| 9,205,240 B2 | 12/2015 | Greenhalgh et al. |
| 9,308,584 B2 | 4/2016 | Burgess et al. |
| 9,310,812 B2 | 4/2016 | Costle et al. |
| 9,375,533 B2 | 6/2016 | Ducharme et al. |
| 9,492,646 B2 | 11/2016 | Hoogenakker et al. |
| 9,517,976 B2 | 12/2016 | Mackal |
| 9,545,490 B2 | 1/2017 | Iwatschenko et al. |
| 9,555,185 B2 | 1/2017 | Foster et al. |
| 9,629,966 B2 | 4/2017 | Ji |
| 9,636,470 B2 | 5/2017 | Pohlmann et al. |
| 9,707,359 B2 | 7/2017 | Kubo |
| 9,713,682 B2 | 7/2017 | Eistetter et al. |
| 9,717,821 B2 | 8/2017 | Schutte et al. |
| 9,717,897 B2 | 8/2017 | Rogier |
| 9,821,084 B2 | 11/2017 | Diegelmann et al. |
| 9,839,772 B2 | 12/2017 | Ducharme |
| 9,839,774 B2 | 12/2017 | Bonaldo |
| 9,846,439 B2 | 12/2017 | Carman et al. |
| 9,867,931 B2 | 1/2018 | Gittard |
| 9,976,660 B2 | 5/2018 | Stanton et al. |
| 10,004,690 B2 | 6/2018 | Lee et al. |
| 10,010,705 B2 | 7/2018 | Greenhalgh et al. |
| 10,017,231 B2 | 7/2018 | Fawcett, Jr. |
| 10,036,617 B2 | 7/2018 | Mackal |
| 10,065,004 B2 | 9/2018 | Eder et al. |
| 10,173,019 B2 | 1/2019 | Kaufmann et al. |
| 10,384,049 B2 | 8/2019 | Stanton et al. |
| 10,420,794 B2 | 9/2019 | Medina et al. |
| 10,463,811 B2 | 11/2019 | Lee et al. |
| 10,507,293 B2 | 12/2019 | Goodman et al. |
| 10,646,706 B2 | 5/2020 | Rogier |
| 10,730,595 B2 | 8/2020 | Fawcett |
| 10,751,523 B2 | 8/2020 | Rogier |
| 10,786,596 B2 * | 9/2020 | Fredrickson ......... A61K 31/722 |
| 10,806,853 B2 | 10/2020 | Gittard |
| 10,850,814 B2 | 12/2020 | Fawcett |
| 10,994,818 B2 | 5/2021 | Hernandez |
| 2004/0107963 A1 | 6/2004 | Finlay et al. |
| 2004/0249359 A1 | 12/2004 | Palasis et al. |
| 2005/0121025 A1 | 6/2005 | Gamard et al. |
| 2005/0123485 A1 | 6/2005 | Suzuki |
| 2005/0147656 A1 | 7/2005 | McCarthy et al. |
| 2005/0220721 A1 | 10/2005 | Kablik et al. |
| 2005/0284809 A1 | 12/2005 | Looney et al. |
| 2006/0004314 A1 | 1/2006 | McCarthy et al. |
| 2006/0213514 A1 | 9/2006 | Price et al. |
| 2007/0056586 A1 | 3/2007 | Price et al. |
| 2007/0066920 A1 | 3/2007 | Hopman et al. |
| 2007/0066924 A1 | 3/2007 | Hopman et al. |
| 2007/0082023 A1 | 4/2007 | Hopman et al. |
| 2007/0125375 A1 | 6/2007 | Finlay et al. |
| 2007/0151560 A1 | 7/2007 | Price et al. |
| 2007/0083137 A1 | 8/2007 | Hopman et al. |
| 2007/0199824 A1 | 8/2007 | Hoerr et al. |
| 2008/0021374 A1 | 1/2008 | Kawata |
| 2008/0287907 A1 | 11/2008 | Gregory et al. |
| 2009/0101144 A1 | 4/2009 | Gamard et al. |
| 2009/0155342 A1 | 6/2009 | Diegemann et al. |
| 2009/0159422 A1 | 6/2009 | Seo et al. |
| 2009/0281486 A1 | 11/2009 | Ducharme |
| 2010/0121261 A1 | 5/2010 | Kablik et al. |
| 2010/0305505 A1 | 12/2010 | Ducharme et al. |
| 2011/0066132 A1 | 3/2011 | Ji |
| 2011/0073200 A1 | 3/2011 | Overvaag et al. |
| 2011/0274726 A1 | 11/2011 | Guo et al. |
| 2011/0308516 A1 | 12/2011 | Price et al. |
| 2012/0108509 A1 | 5/2012 | Hissong et al. |
| 2014/0271491 A1 | 9/2014 | Gittard et al. |
| 2015/0094649 A1 | 4/2015 | Gittard |
| 2015/0125513 A1 | 5/2015 | McCarthy |
| 2016/0375202 A1 | 12/2016 | Goodman et al. |
| 2017/0106181 A1 | 4/2017 | Bonaldo et al. |
| 2017/0232134 A1 | 8/2017 | Clare et al. |
| 2017/0232141 A1 | 8/2017 | Surti et al. |
| 2017/0252479 A1 | 9/2017 | Ji et al. |
| 2017/0296760 A1 | 10/2017 | Lee et al. |
| 2018/0099088 A1 | 4/2018 | Gittard |
| 2018/0193574 A1 | 7/2018 | Smith et al. |
| 2018/0214160 A1 | 8/2018 | Hoskins et al. |
| 2018/0339144 A1 | 11/2018 | Greenhalgh et al. |
| 2019/0134366 A1 | 5/2019 | Erez et al. |
| 2019/0217315 A1 | 7/2019 | Maguire et al. |
| 2019/0232030 A1 | 8/2019 | Pic et al. |
| 2021/0024187 A1 | 1/2021 | Fawcett et al. |
| 2021/0069485 A1 | 3/2021 | Rogier |

FOREIGN PATENT DOCUMENTS

| | | |
|---|---|---|
| CN | 101401956 B | 11/2012 |
| DE | 60215438 T2 | 8/2007 |
| EP | 3081236 A1 | 10/2016 |
| EP | 3052168 B1 | 11/2019 |
| JP | H07118305 A | 5/1995 |
| JP | 2011518839 A | 6/2011 |
| WO | 03013552 A1 | 2/2003 |
| WO | WO 03/013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | WO 2007/074327 A1 | 7/2007 |
| WO | 2008033462 A2 | 3/2008 |
| WO | WO 2009/028965 A1 | 3/2009 |
| WO | 2009061409 A1 | 5/2009 |
| WO | WO 2009/132224 A2 | 10/2009 |
| WO | WO 2012/058312 A1 | 5/2012 |
| WO | WO 2013/053753 A2 | 4/2013 |
| WO | WO 2014/191738 A1 | 12/2014 |

(56) References Cited

FOREIGN PATENT DOCUMENTS

| WO | 2015050814 A1 | 4/2015 |
|---|---|---|
| WO | WO 2016/109847 A1 | 7/2016 |
| WO | 2018157772 A1 | 9/2018 |

OTHER PUBLICATIONS

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

International Search Report and Written Opinion for application No. PCT/US2019/013179, dated Apr. 24, 2019, 14 pages.

Author unknown, Database WPI/Clarivate Analytics, week Feb. 12, 2014, Thompson Scientific, London GB XP-002790475, 2 pages.

Fernandes, M. et al., "Modulation of stability and mucoadhesive properties of chitosan microspheres for therapeutic gastric application," International Journal of Pharmaceutics, vol. 454, pp. 116-124 (2013).

Bedel, N. S. et al., "Effects of pore morphology and size on antimicrobial activity of chitosan/poly(ethylene glycol) diacrylate macromere semi-IPN hydrogels," Journal of Applied Polymer Science, vol. 132, pp. 1-10 (2015).

Gamiz Gonzalez, M. A. et al., "Synthesis of highly swellable hydrogels of water-soluble carboxymethyl chitosan and poly(ethylene glycol)," Polymer International, vol. 66, pp. 1624-1632 (2017).

Kono, H., "Characterization and properties of carboxymethyl cellulose hydrogels crosslinked by polyethylene glycol," Carbohydrate Polymers, vol. 106, pp. 84-93 (2014).

Lee, S. J. et al., "Interpenetrating polymer network hydrogels based on poly(ethylene glycol) macromer and chitosan," Carbohydrate Polymers, vol. 41, pp. 197-205 (2000).

Lee, Y. M. et al., "Synthesis and properties of poly(ethylene glycol) macromer/β-chitosan hydrogels," Journal of Materials Science: Materials in Medicine, vol. 8, pp. 537-541 (1997).

Li, H., Packaging Applied Chemistry, p. 138, Beijing: GCP, Jan. 2014 (5 pages).

Liao, X., "Experiment 31 Synthesis of novel chitosan in situ hydrogels," Guidance on Basic Experiments in Materials Chemistry, p. 78, Beijing: Metallurgical Industry Press, Feb. 2015 (6 pages).

Saladino, S. et al., "Formulation of Different Chitosan Hydrogels for Cartilage Tissue Repair," Chemical Engineering Transactions, vol. 38, pp. 505-510 (2014).

\* cited by examiner

POWDER FOR ACHIEVING HEMOSTASIS

CROSS-REFERENCE TO RELATED APPLICATIONS

This application is a continuation of U.S. application Ser. No. 16/245,780, filed Jan. 11, 2019, which claims the benefit of U.S. Provisional Application No. 62/616,751, filed Jan. 12, 2018, entitled "Powder for Achieving Hemostasis," the disclosure of each of which is hereby incorporated by reference in its entirety.

BACKGROUND

Gastrointestinal bleeding affects millions of people annually. Certain cases of internal bleeding cannot be controlled effectively by current hemostatic technologies such as clips, cautery, or band ligation. Wounds, surgical sites, diseased tissue, ulcer beds and gastric varices, among others, are locations where conventional means of hemostasis may to fail, leading to extended hospital stay or death.

SUMMARY

In various aspects, the present disclosure pertains to methods of treating or preventing bleeding at a tissue site comprising applying a chitosan powder composition to the tissue site, wherein the chitosan powder composition comprises a chitosan salt, a crosslinked chitosan, a derivatized chitosan, or a combination thereof.

In various embodiments, the tissue site may be a body lumen, for example a site in the gastrointestinal tract. When the tissue site is a body lumen, the chitosan powder may be applied, for example, via a catheter or other suitable device.

In various embodiments, which may be used in conjunction with the above aspects and embodiments, the powder may be fluidized in a gas (e.g., $CO_2$, nitrogen, air, etc.) to form a fluidized powder and blown onto the tissue site. In such embodiments, the fluidized powder may exit the catheter at a velocity ranging from 15 to 50 m/s, among other possible velocities.

In various aspects, the present disclosure pertains to powder compositions for application to a tissue site, where the powder compositions comprise first particles comprising chitosan, a chitosan salt or a derivatized chitosan admixed with second particles that comprise a crosslinking agent that covalently or non-covalently interacts with the first particles upon exposure to moisture.

In some embodiments, the first particles may comprise a chitosan salt and the crosslinking agent may be a polyanionic crosslinking agent. For example, the first particles may comprise chitosan or a chitosan salt and the crosslinking agent may be a covalent crosslinking agent. Examples of covalent crosslinking agents include, for instance, a multifunctional epoxy, a multifunctional aldehyde, multifunctional acrylate, genipin, or a derivatized polymer (e.g., an aldehyde derivatized polymer, an epoxy derivatized polymer, acrylate derivatized polymer or a genipin derivatized polymer), among other possibilities.

In some embodiments, which may be used in conjunction with the above aspects and embodiments, the first particles may comprise a derivatized chitosan and the second particles may comprise a covalent crosslinking agent. In one particular example, the first particles may comprise thiol-modified chitosan and the second particles may comprise a molecule having a plurality of unsaturated groups.

In various aspects, the present disclosure pertains to powder compositions for application to a tissue site that comprise derivatized chitosan.

In some embodiments, the derivatized chitosan reacts with cysteine groups in tissue upon exposure to moisture. For example, the derivatized chitosan may be chitosan derivatized with a multifunctional aldehyde, the derivatized chitosan may be chitosan derivatized with a multifunctional epoxide, the derivatized chitosan may be chitosan derivatized with a multifunctional acrylate, or the derivatized chitosan may be chitosan derivatized with genipin.

In some embodiments, which may be used in conjunction with the above aspects and embodiments, the derivatized chitosan may interact with thiol groups in tissue upon exposure to moisture.

In some embodiments, which may be used in conjunction with the above aspects and embodiments, the derivatized chitosan may be chitosan derivatized with unsaturated groups or the derivatized chitosan may be derivatized with thiol groups, among other possibilities.

In various aspects, the present disclosure pertains to powder compositions for application to a tissue site that comprise a chitosan salt.

In some embodiments, the chitosan salt ionically crosslinks with negative charged species in tissue or blood.

In various aspects, which may be used in conjunction with the above aspects and embodiments, the disclosure pertains to catheter assemblies, which are preloaded with a chitosan powder composition and which are configured to deliver the chitosan powder composition a tissue site.

These and other aspects and embodiments are further described in the detailed description to follow.

DETAILED DESCRIPTION

In various aspects, the present disclosure pertains to methods of treating a tissue site (e.g., a wound, a surgical site, a diseased tissue site, an ulcer bed, a gastric varix, etc.), in which a chitosan powder is applied to the tissue site. The chitosan powder may be applied, for example, to address existing bleeding or to prevent or minimize future bleeding that may occur. In various embodiments, the tissue site is tissue that surrounds a body lumen, for example, a wall of the gastrointestinal tract. The chitosan powder may contain, for example, chitosan, a chitosan salt, crosslinked chitosan, derivatized chitosan, or natural or synthetic polymer blends containing the same. As discussed in more detail below, in particular embodiments, the chitosan powder may comprise, for example, a chitosan salt, a crosslinked chitosan a derivatized chitosan or a combination thereof.

In various embodiments, the chitosan powder may be applied to a tissue site via a catheter. Examples include catheter assemblies in which a powder may be fluidized in a gas (e.g., compressed air, nitrogen, carbon dioxide, etc.) to form fluidized powder, which is then blown onto the tissue site. For example, a catheter assembly may be provided, which includes (a) a catheter having a lumen extending therethrough, a proximal end, and a distal end having an exit orifice, and (b) a reservoir containing a chitosan powder. The catheter assembly may be configured to deliver the chitosan powder from the reservoir, through the lumen, and out the exit orifice. In certain embodiments, the catheter assembly may include a pressurized reservoir that contains a pressurized gas for delivering the chitosan powder from the reservoir, through the lumen, and out the exit orifice. For example, the pressurized reservoir may be positioned upstream of the reservoir and the pressurized gas passed through the chitosan powder, thereby fluidizing the chitosan powder in the gas for delivery of through the lumen and out the exit orifice. In certain embodiments, the catheter is operated such that the fluidized powder exits the catheter at a velocity ranging from 15 m/s to 50 m/s. Where applied to the gastrointestinal tract, the chitosan powder may be applied through an endoscope.

In various aspects, the present disclosure pertains to catheters that are preloaded with a chitosan powder. For example, a system may be provided, which includes a catheter having a proximal end and a distal end that is partially loaded with chitosan powder (with a remaining volume being air). The catheter may also include a seal, such as a plug, cap, or other mechanism for retaining the chitosan powder on the proximal and distal ends of the catheter. The system may further be provided with a mechanism for breaking the proximal seal and for applying gas to the catheter at sufficient pressure to fluidize the powder in the catheter, eject the distal seal, and disperse the fluidized chitosan powder from the distal end of the catheter and onto the treatment site.

When applied to a tissue site, chitosan powder in accordance with the present disclosure acts as a barrier to bleeding associated with the tissue site. The chitosan powder acts as a barrier by absorbing liquids, which, for example, may be bodily fluids such as blood or gastrointestinal fluids (e.g., pancreatic juices, biliary fluid, saliva, etc.) that are present at the tissue site, or may be fluid such as saline, phosphate buffered saline, or contrast fluid that is applied to the tissue site prior to, concurrently with, or subsequent to application of the chitosan powder. The chitosan powder may be used to achieve hemostasis at sites of active bleeding or can be used as a preventative over clipped areas, suture sites, or other having the potential for bleeding, among other uses.

In various aspects, the present disclosure pertains to chitosan powders, that may be used to for hemostasis, among other possible uses.

Chitosan powders for use in the present disclosure may be of any suitable particle size. In various embodiments, the particle size may range, for example, from less than 1 μm to 1000 μm (e.g., ranging from 1 μm to 2.5 μm to 5 μm to 10 μm to 25 μm to 50 μm to 100 μm to 250 μm to 500 μm to 1000 μm), among other possibilities. In this regard, a chitosan powder having particles sized between 50 μm and 425 μm performs well when dispensed through an 8 French catheter.

As noted above, chitosan powder may contain, for example, chitosan, a chitosan salt, derivatized chitosan, or crosslinked chitosan, and, optionally, a natural or synthetic polymer.

Chitosan is a modified polysaccharide containing randomly distributed β-(1-4)-linked D-glucosamine and N-acetyl-D-glucosamine monomer units. Chitosan is produced commercially by the alkaline N-deacetylation of chitin, which is a cellulose-like polymer consisting primarily of unbranched chains of modified glucose, specifically N-acetyl-D-glucosamine.

The degree of deacetylation in commercial chitosans typically ranges from 75 to 100% although essentially any degree of deacetylation is possible. Chitosan is positively charged in acidic to neutral solutions with a charge density that is dependent on the pH and the degree of deacetylation. The pka value of chitosan generally ranges from 6.1 to 7.0, depending on the degree of deacetylation. Thus, while typically substantially insoluble in distilled water, chitosan is generally soluble in aqueous acidic solutions (e.g., pH ~6.5 or less).

Examples of chitosan salts include chitosan halides such as chitosan fluoride, chitosan chloride, chitosan bromide, chitosan iodide, chitosan phosphate, chitosan nitrate, chitosan sulfate, chitosan salts of organic mono-acids such as formate, acetate, propionate, butyrate, chitosan salts of organic diacids such as oxalate, malonate, succinate, maleate, or glutarate, or salts of hydroxyacids such as glycolate, lactate, tartrate, malate, citrate, or gluconate.

In various embodiments, modified chitosans may be employed, which exhibit enhanced properties, including enhanced adhesion. For instance, a thiol-modified chitosan may be formed by reaction of chitosan with a molecule having one or more thiol groups and one or more additional groups (e.g., carboxylic acid groups, which may also be referred to herein as carboxyl groups) for bonding to the chitosan. In a specific example, carboxylic acid groups of thiolactic acid may be reacted with primary amine groups on the chitosan through suitable chemistry to form a covalent amide bond. For example, carbodiimide conjugation works by activating carboxylic acid groups with a suitable carbodiimide, such as 1-ethyl-3-(3-dimethylaminopropyl)carbodiimide (EDC), dicyclohexylcarbodiimide (DCC), N,N'-diisopropylcarbodiimide (DIC), for direct conjugation to primary amines (e.g., primary amine groups on the chitosan) via amide bond formation. Similarly, carbonyldiimidazole (CDI) can be used in non-aqueous conditions to activate carboxylic acids for direct conjugation to primary amines (e.g., primary amine groups on the chitosan) via amide bonds. The thiols on the modified chitosan can provide enhanced attachment by interacting and forming covalent bonds with cysteine-rich tissue.

Other examples of modified chitosans include chitosan modified with groups that allow for covalent reaction with tissue, including groups that are reactive with amine groups found in tissue. For example, a multifunctional (e.g., difunctional, trifunctional, etc.) reactive molecule such as a multifunctional aldehyde molecule can be reacted with amine groups on chitosan to form aldehyde-modified chitosan (chitosan having pendant aldehyde groups). As another example, a multifunctional (e.g., difunctional, trifunctional, etc.) reactive molecule, such as a multifunctional epoxide molecule, can be reacted with amine groups on chitosan to form epoxy-modified chitosan (i.e., chitosan having pendant epoxide groups). As another example, a multifunctional (e.g., difunctional, trifunctional, etc.) reactive molecule, such as a multifunctional acrylate molecule or another molecule having one or more groups that react with chitosan and has at least one acrylate group such as PEG diacrylate, can be reacted with thiol groups on thiol modified chitosan via michael addition click reaction under body temperature in physiological pH conditions to form a chitosan-PEG crosslinked network (i.e., chitosan-PEG crosslinked gel having excess pendant thiol groups amendable to covalently linking to tissue). As another example, a multifunctional (e.g., difunctional, trifunctional, etc.) reactive molecule, such as genipin, can be reacted with amine groups on chitosan to form genipin-modified chitosan (i.e., chitosan having pendant genipin groups). In certain specific embodiments, the multifunctional reactive molecule (e.g., multifunctional aldehyde molecule, a multifunctional epoxide molecule, or genipin) may be reacted with chitosan in relative amounts such that multifunctional reactive molecule is provided in a 1× molar minimum relative to the number of moles of amine groups on the chitosan, such that all or essentially all of the amine groups are reacted and have pendant reactive groups.

Example of multifunctional aldehydes include glutaraldehyde, glyoxal, and aldehyde terminated hydrophilic polymers. Example of multifunctional epoxides include 4-butanediol diglycidyl ether, ethylene glycol diglycidyl ether, and epoxide terminated hydrophilic polymers. Hydrophilic polymers which may be provided with aldehyde or epoxide termination include poly(ethylene glycol) (PEG), also referred to as poly(ethylene oxide) (PEO), polyvinyl alcohol (PVA), polyvinyl pyrrolidone (PVP), polyacrylamide, poly(acrylic acid), and poly(hydroxyethyl methacrylate) (PHEMA), Suitable hydrophilic polymers may range, for example, from 2 to 250 monomers in length, among other possibilities.

In certain specific embodiments, a modified chitosan may be formed by reacting a reactive synthetic molecule such as PEG diepoxide or a PEG dialdehyde with chitosan in relative amounts such that the reactive molecule is provided in a 1× molar minimum relative to the number of moles of amine groups on the chitosan, such that all or essentially all of the amine groups of the chitosan are reacted and have pendant epoxide-terminated PEG groups or aldehyde-terminated PEG groups.

In some embodiments, the chitosan may be directly oxidized, thereby forming aldehyde groups on the chitosan.

In some embodiments, a chitosan powder may be employed in which chitosan, chitosan salt, modified chitosan, or a combination thereof, is non-covalently crosslinked or covalently crosslinked, either before application to a tissue site, or at the time of application to a tissue site.

For instance, in some embodiments, an ionic crosslinker such as a multifunctional anionic molecule having two or more anionic groups (e.g., carboxylic acid groups, or sulfonate groups) may be provided in order to ionically crosslink the chitosan via positively charged amine groups located on the chitosan, Examples of multifunctional anionic molecules include organic diacids such as oxalate, malonate, succinate, maleate, or glutarate, or salts of hydroxyacids such as tartrate, malate, or citrate. Examples of multifunctional anionic molecules also include polyanionic polymers.

In some embodiments, the multifunctional anionic molecule is combined and ionically crosslinked with the chitosan prior to applying to tissue, grinding the crosslinked product into a powder if desired or necessary. In some embodiments, the multifunctional anionic molecule is ionically crosslinked on the tissue surface. For example, a multifunctional anionic molecule (e.g., citric acid, among others) may be combined with chitosan in powder form and the mixture applied to tissue. When this mixture contacts a moisture rich environment (e.g., provided by body fluid and/or a separately applied fluid), liquid will be absorbed and the powder constituents will dissolve and crosslink, creating a firmer more cohesive gel with less particulate over the application site.

In some embodiments, chitosan or modified chitosan may be covalently crosslinked prior to administration, and subsequently applied to tissue. For instance, chitosan or modified chitosan may be reacted with a multifunctional molecule having two or more groups (e.g., carboxylic acid groups, amine groups, epoxy groups, or aldehyde groups) that are reactive with the chitosan (e.g., reactive with the amine groups on the chitosan or carboxymethyl groups on the modified chitosan). For example, a biocompatible hydrophilic polymer (e.g., one the hydrophilic polymers listed above, among others) having terminal carboxylic acid groups may be reacted with primary amine groups on the chitosan through any suitable chemistry (e.g., using carbodiimide or carbonyldiimidazole chemistry) in order to covalently crosslink the chitosan. In one specific embodiment, carboxylic acid groups of a PEG dicarboxylate may be reacted with amine groups of chitosan using carbodiimide or carbonyldiimidazole chemistry, thereby covalently crosslinking the chitosan. As another example, a derivatized chitosan (e.g., a chitosan derivatized with carboxylic acid groups) is crosslinked with a biocompatible hydrophilic polymer (e.g., one the hydrophilic polymers listed above, among others) having terminal amine groups through any suitable chemistry (e.g., using carbodiimide or carbonyldiimidazole chemistry) in order to covalently crosslink the chitosan. In one specific embodiment, amine groups of a PEG diamine may be reacted with carboxylic acid groups of carboxymethyl chitosan using carbodiimide or carbonyldiimidazole chemistry, thereby covalently crosslinking the chitosan. The resulting product is subsequently applied to tissue, after grinding the product into a powder, if desired or necessary. This should generally improve the overall structural integrity of the powder.

In some embodiments, a chitosan powder is provided, which become covalently crosslinked upon administration to tissue.

For example, a first powder comprising a multifunctional (e.g., difunctional, trifunctional, etc.) reactive molecule that reacts with amines, for example, genipin, a multifunctional aldehyde molecule, or a multifunctional epoxide molecule, such as those described above (e.g., PEG diepoxide, PEG dialdehyde or any small molecule dialdehyde or small molecule diepoxide that is a solid), may be admixed with chitosan or a chitosan salt powder and applied to tissue in dry form. In certain embodiments, the multifunctional reactive molecule is a modified chitosan such as those described above, which may be selected, for example, from the aldehyde-modified chitosan (chitosan having pendant aldehyde groups), epoxy-modified chitosan (i.e., chitosan having pendant epoxide groups) and genipin-modified chitosan (i.e., chitosan having pendant genipin groups) described above. Once the admixed powder becomes wet (e.g., due to body fluid and/or application of a fluid), the powder constituents dissolve, allowing the multifunctional reactive molecule to crosslink with amines found on the chitosan or the chitosan salt, and to also react with amines found in tissue.

As another example, a first powder comprising a thiol-modified chitosan such as that described above may be admixed a second powder that comprises a molecule that comprises two or more unsaturated groups and applied to tissue in dry form. Examples of molecules that comprises two or more unsaturated groups include acrylate-terminated hydrophilic polymers. Hydrophilic polymers which may be provided with unsaturated termination include those hydrophilic polymers described above. A particular example of a molecule that comprises two or more unsaturated groups is PEG diacrylate. Applying such a powder to tissue and subsequently mixing with saline in situ will follow a Michael addition reaction scheme. At body temperature and the pH of saline (7.4) the two powders crosslink to form a cohesive patch. In certain embodiments, the first powder or the second powder may include a catalyst, such as a base or a nucleophile).

Various further aspects of the present disclosure are provided in the following enumerated paragraphs:

Aspect A1. A method of treating or preventing bleeding at a tissue site comprising: applying chitosan powder to the tissue site, wherein the chitosan powder comprises a chitosan salt, a crosslinked chitosan, a derivatized chitosan, or a combination thereof.

Aspect A2. The method of aspect A1, wherein the tissue site is in a body lumen.

Aspect A3. The method of aspect A2, wherein the body lumen is the gastrointestinal tract.

Aspect A4. The method of any of aspects A1-A3, wherein the chitosan powder is applied via a catheter.

Aspect A5. The method of any of aspects A1-A4, wherein the powder is fluidized in a gas to form a fluidized powder and blown onto the tissue site.

Aspect A6, The method of aspect A6, wherein the fluidized gas is $CO_2$.

Aspect A7. The method of any aspects A6-A7, wherein the fluidized powder exits the catheter at a velocity ranging from 15 to 50 m/s.

Aspect B1. A preloaded catheter assembly comprising: a catheter having a lumen extending therethrough, a proximal end, and a distal end having an exit orifice, a reservoir comprising a chitosan powder, wherein the catheter assembly is configured to deliver the chitosan powder from the reservoir, through the lumen, and out the exit orifice.

Aspect B2. The preloaded catheter of aspect B1, wherein the catheter assembly further comprises a pressurized reservoir comprising a pressurized gas for delivering the chitosan powder from the reservoir, through the lumen, and out the exit orifice.

Aspect B3. The preloaded catheter of aspect B2, wherein the pressurized reservoir is positioned upstream of the reservoir and the pressurized gas passes through the chitosan powder, thereby fluidizing the chitosan powder in gas for delivery of through the lumen and out the exit orifice.

Aspect B4. The preloaded catheter of aspect B1, the chitosan powder comprises chitosan, a chitosan salt, crosslinked chitosan, derivatized chitosan, or a combination thereof.

Aspect C1. A powder composition for application to a tissue site, the powder composition comprising first particles comprising chitosan, a chitosan salt or a derivatized chitosan admixed with second particles that comprise a crosslinking agent that covalently or non-covalently interacts with the first particles upon exposure to moisture.

Aspect C2. The composition of aspect C1, wherein the first particles comprise a chitosan salt.

Aspect C3. The composition of aspect C2, wherein the crosslinking agent is a polyanionic crosslinking agent.

Aspect C4. The composition of aspect C1, wherein the first particles comprise chitosan or a chitosan salt and the crosslinking agent is a covalent crosslinking agent.

Aspect C5. The composition of aspect C4, wherein the covalent crosslinking agent is selected from a multifunctional epoxy, a multifunctional aldehyde, and genipin.

Aspect C6. The composition of aspect C4, wherein the covalent crosslinking agent is a derivatized polymer.

Aspect C7. The composition of aspect C6, wherein the derivatized polymer is selected from an aldehyde derivatized polymer, epoxy derivatized polymer, and a genipin derivatized polymer.

Aspect C8. The composition of aspect C6, wherein the derivatized polymer is derivatized chitosan.

Aspect C9. The composition of aspect C8, wherein the derivatized chitosan selected from aldehyde derivatized chitosan, epoxy derivatized chitosan, and genipin derivatized chitosan.

Aspect C10. The composition of aspect C1, wherein the first particles comprise a derivatized chitosan.

Aspect C11. The composition of aspect C10, wherein the second particles comprise a covalent crosslinking agent.

Aspect C12. The composition of aspect C11, wherein the covalent crosslinking agent is a polymeric crosslinking agent.

Aspect C13. The composition of aspect C10, wherein the first particles comprise thiol-modified chitosan and the second particles comprise a molecule having a plurality of unsaturated groups.

Aspect C14. The composition of aspect C13, wherein the molecule having a plurality of unsaturated groups is a hydrophilic polymer having unsaturated end groups.

Aspect D1. A powder composition for application to a tissue site, the powder composition comprising chitosan crosslinked with a multifunctional carboxylated polymer.

Aspect D2. The composition of aspect D1, wherein the carboxylated polymer is a hydrophilic polymer having carboxylic acid end groups.

Aspect D3. The composition of aspect D1 or D2, chitosan is crosslinked with the multifunctional carboxylated polymer using a diimide coupling.

Aspect E1. A powder composition for application to a tissue site, the powder composition comprising derivatized chitosan.

Aspect E2. The powder of aspect E1, wherein the derivatized chitosan reacts with tissue upon exposure to moisture.

Aspect E3. The powder of aspect E1, wherein the derivatized chitosan reacts with primary amine groups in tissue upon exposure to moisture.

Aspect E4. The powder of aspect E2, wherein the derivatized chitosan is chitosan derivatized with a multifunctional aldehyde.

Aspect E5. The powder of aspect E2, wherein the derivatized chitosan is chitosan derivatized with a multifunctional epoxide.

Aspect E6. The powder of aspect E2, wherein the derivatized chitosan is chitosan derivatized with genipin.

Aspect E7. The powder of aspect E1, wherein the derivatized chitosan interacts with thiol groups in tissue upon exposure to moisture.

Aspect E8. The powder of aspect E7, wherein the derivatized chitosan is chitosan derivatized with unsaturated groups.

Aspect E9. The powder of aspect E7, wherein the derivatized chitosan is derivatized with thiol groups.

Aspect E10. The powder of aspect E9, wherein the chitosan is derivatized with a compound comprising a carboxylic acid group and a thiol group.

Aspect E11. The powder of aspect E10, wherein the chitosan is derivatized using diimide (e.g., EDC or DCC) coupling.

EXAMPLE

Chitosan obtained from Sigma Aldrich is suspended in water at a concentration of 2 wt % Chitosan and 98 wt % water. The mixture is stirred using a mechanical mixer at room temperature. Acetic acid is then added during the stirring such that the pH levels out near 5.0 after 5 hours of stirring. 2 wt % citric acid (relative to the weight of chitosan initially used) is added to the container and mixed for an additional 5 hours. This process forms a gel which is subsequently dried. The dried gel is then ground into a fine powder for use.

The invention claimed is:

1. A method of treating a tissue site comprising:
   administering a composition to the tissue site;
   wherein the composition includes a powder that comprises first particles comprising chitosan or a chitosan salt and second particles that comprise a crosslinking agent, wherein the crosslinking agent is a derivatized polymer selected from an epoxy derivatized polymer, an acrylate derivatized polymer, or a genipin derivatized polymer.

2. The method of claim 1, wherein the composition is applied via a catheter.

3. The method of claim 1, wherein the composition is fluidized in a gas to form a fluidized powder and blown onto the tissue site.

4. The method of claim 3, wherein the gas is $CO_2$.

5. The method of claim 3, wherein the fluidized powder is applied using a catheter and wherein the fluidized powder exits the catheter at a velocity ranging from 15 m/s to 50 m/s.

6. A composition comprising:
first particles comprising chitosan or a chitosan salt; and
second particles comprising a crosslinking agent, wherein the crosslinking agent is selected from an epoxy derivatized polymer, an acrylate derivatized polymer, a genipin derivatized polymer, a multifunctional epoxy, acrylate, or genipin.

7. The composition of claim 6, wherein the crosslinking agent is the epoxy derivatized polymer or the acrylate derivatized polymer.

8. The composition of claim 6, wherein the first particles comprise a chitosan salt, wherein the chitosan salt comprises a chitosan halide, a chitosan salt of an organic mono-acid, or a chitosan salt of an organic diacid.

9. The composition of claim 6, wherein the epoxy derivatized polymer is epoxy derivatized chitosan, the acrylate derivatized polymer is acrylate derivatized chitosan, and the genipin derivatized polymer is genipin derivatized chitosan.

10. A method of treating or preventing bleeding at a tissue site comprising applying the composition of claim 6 to a gastrointestinal tract through an endoscope.

11. The method of claim 10, wherein the composition is fluidized in a gas to form a fluidized powder composition and blown onto the tissue site.

12. The method of claim 11, wherein the gas is $CO_2$.

13. The method of claim 11, wherein the fluidized powder exits the endoscope at a velocity ranging from 15 m/s to 50 m/s.

14. A composition comprising:
first particles comprising a modified chitosan selected from an aldehyde modified chitosan, epoxy modified chitosan, chitosan modified with unsaturated groups, chitosan derivatized with a multifunctional epoxide, acrylate modified chitosan, or thiol-modified chitosan; and
second particles comprising a covalent crosslinking agent;
wherein the composition is in the form of a powder; and
wherein the covalent crosslinking agent is a molecule having a plurality of unsaturated groups when the first particles comprise thiol-modified chitosan.

15. The composition of claim 14, wherein the molecule having a plurality of unsaturated groups comprises a hydrophilic polymer having unsaturated end groups.

16. The composition of claim 14, wherein the covalent crosslinking agent is a hydrophilic polymer having terminal carboxylic acid groups or terminal amine groups when the first particles comprise aldehyde modified chitosan, epoxy modified chitosan, chitosan modified with unsaturated groups, chitosan derivatized with a multifunctional epoxide, acrylate modified chitosan; and
wherein the covalent crosslinking agent is a molecule including an acrylate-terminated hydrophilic polymer when the first particles comprise thiol-modified chitosan.

17. A method of treating or preventing bleeding at a tissue site comprising applying the composition of claim 14 to a gastrointestinal tract through an endoscope.

18. The method of claim 17, wherein the composition is fluidized in a gas to form a fluidized powder and blown onto the tissue site.

19. The method of claim 18, wherein the gas is $CO_2$.

20. The method of claim 18, wherein the fluidized powder exits the endoscope at a velocity ranging from 15 m/s to 50 m/s.

* * * * *